United States Patent [19]

Arabori et al.

[11] Patent Number: 5,059,238

[45] Date of Patent: Oct. 22, 1991

[54] N-SUBSTITUTED-3-(SUBSTITUTED HYDRAZINO)-BENZENESULFONAMIDE DERIVATIVES, AND HERBICIDAL COMPOSITIONS

[75] Inventors: Hideo Arabori; Shiro Yamazaki; Masato Arahira; Aiko Murakami, all of Iwaki, Japan

[73] Assignee: Kureha Kagaku Kogyo K.K., Tokyo, Japan

[21] Appl. No.: 473,768

[22] Filed: Feb. 2, 1990

[30] Foreign Application Priority Data

Feb. 8, 1989 [JP] Japan ..................... 1-27369

[51] Int. Cl.$^5$ .................. C07D 251/42; C07D 251/46; A01N 43/66
[52] U.S. Cl. ........................... 71/93; 544/211
[58] Field of Search ........................ 71/93; 544/211

[56] References Cited

U.S. PATENT DOCUMENTS

| | | | |
|---|---|---|---|
| 4,585,470 | 4/1986 | Petersen | 71/92 |
| 4,632,695 | 12/1986 | Schurter et al. | 71/93 |
| 4,664,695 | 5/1987 | Schurter et al. | 71/92 |
| 4,678,497 | 7/1987 | Petersen | 71/92 |

FOREIGN PATENT DOCUMENTS 162723 5/1985 European Pat. Off. .
62-129276 6/1987 Japan .

Primary Examiner—John M. Ford
Attorney, Agent, or Firm—Lowe, Price, LeBlanc & Becker

[57] ABSTRACT

Disclosed herein are N-substituted-3-(substituted hydrazino)benzenesulfonamide derivatives of the formula (I):

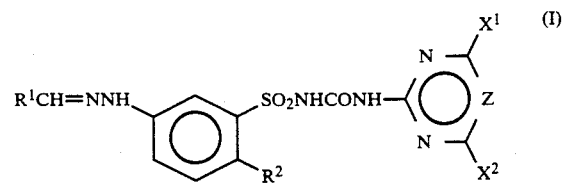

wherein $R^1$ is $CF_3$, COOH or CCl=CClCCOOH, $R^2$ is H, Cl, $C_1$–$C_3$ alkyl or $C_1$–$C_4$ alkoxycarbonyl; Z is CH or N; $X^1$ is $C_1$–$C_3$ alkyl, $C_1$–$C_3$ alkoxyl or Cl; and $X^2$ is $C_1$–$C_3$ alkyl or $C_1$–$C_3$ alkoxyl, a process for the preparation thereof, and herbicidal compositions containing the N-substituted-3-(substituted hydrazino)benzenesulfonamide derivatives as active ingredients.

8 Claims, No Drawings

N-SUBSTITUTED-3-(SUBSTITUTED HYDRAZINO)-BENZENESULFONAMIDE DERIVATIVES, AND HERBICIDAL COMPOSITIONS

BACKGROUND OF THE INVENTION

1) Field of the Invention

The present invention relates to N-substituted-3-(substituted hydrazino)benzenesulfonamide derivatives, a preparation process thereof, and herbicidal compositions containing the derivatives as active ingredients.

2) Description of the Related Art

Numerous compounds have heretofore been proposed as herbicides. For example, U.S. Pat. Nos. 4,632,695, 4,664,695 and Japanese Patent Application Laid-Open (KOKAI) No. 129276/1987 disclose a wide variety of compounds, including N-substituted-3-substituted benzenesulfonamide derivatives containing $NHC(CH_3)=CHCOCH_3$, $NHC(CH_3)=CHCOOCH_3$, $NHCH_3$, $OCH_2CF_3$ or $SCH_2CF_3$ on the 3-position and a pyrimidine ring or a 1,3,5-triazine ring on the nitrogen atom.

There have conventionally been strong demands for herbicides capable of exhibiting reliable herbicidal activity even at such low application dosages as bringing about the advantage of reducing the amount present in the environment, herbicides capable of exhibiting selectivity between crops and weeds irrespective of variations in environmental conditions, herbicides free from crop injury to the second crop in double cropping, etc. The present invention has been completed with a view toward meeting such demands.

The present inventors have found that compounds still unreported to date and having a substituted hydrazino group on the 3-position of benzenesulfonamide as opposed to the inclusion of $NHC(CH_3)=CHCOCH_3$, $NHC(CH_3)=CHCOOCH_3$, $NHCH_3$, $OCH_2CF_3$ or $SCH_2CF_3$ on the 3-position of benzenesulfonamide in the compounds disclosed in EP-A-116518 and Japanese Patent Application Laid-Open (KOKAI) No. 129276/1987 have excellent herbicidal activity, leading to the completion of the present invention.

SUMMARY OF THE INVENTION

Therefore, an object of the invention is to provide novel compounds which show excellent herbicidal activity.

Another object of the invention is to provide a process for preparing novel compounds which show excellent herbicidal activity.

A further object of the invention is to provide intermediates useful in the preparation of novel compounds which show excellent herbicidal activity.

A still further object of the invention is to provide novel herbicidal compositions which show excellent herbicidal activity.

A still further object of the invention is to provide a method for controlling monocotyledonous or dicotyledonous weeds on an agricultural or non-agricultural land.

In one aspect of the invention, there is thus provided an N-substituted-3-(substituted hydrazino)benzenesulfonamide derivative of the formula (I):

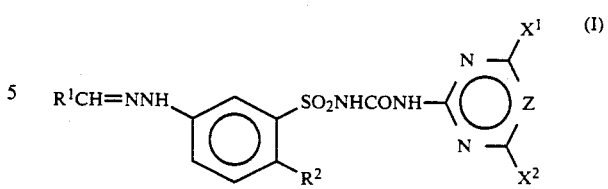

wherein $R^1$ is $CF_3$, COOH or $CCl=CClCOOH$, $R_2$ is H, Cl, $C_1-C_3$ alkyl or $C_1-C_4$ alkoxycarbonyl; Z is CH or N; $X^1$ is $C_1-C_3$ alkyl, $C_1-C_3$ alkoxyl or Cl; and $X^2$ is $C_1-C_3$ alkyl or $C_1-C_3$ alkoxyl.

In another aspect of the invention, there is also provided a process for the preparation of the above-described N-substituted-3-(substituted hydrazino)benzenesulfonamide derivative, which comprises reacting a 3-(substituted hydrazino)benzenesulfonamide derivative of the formula (II):

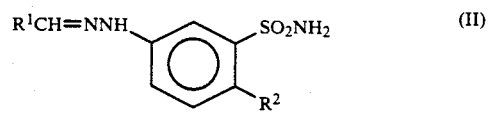

wherein $R^1$ and $R^2$ have the same meanings as defined above, with a phenylcarbamate derivative of the following formula (III):

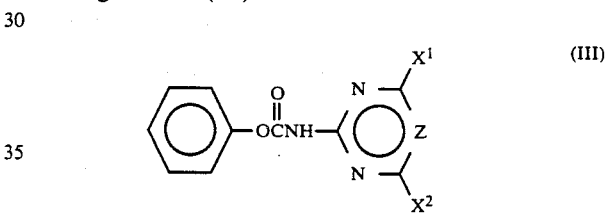

wherein Z, $X^1$ and $X^2$ have the same meanings as defined above.

In a further aspect of the invention, there is also provided a 3-(substituted hydrazino)benzenesulfonamide derivative useful as an intermediate in the preparation of the above N-substituted-3-(substituted hydrazino)benzenesulfonamide, which is represented by the following formula (II):

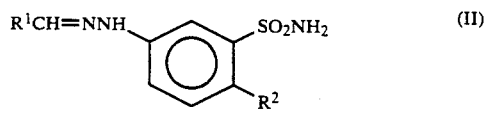

wherein $R^1$ and $R^2$ have the same meanings as defined above.

In a still further aspect of the invention, there is also provided a 3-hydrazinobenzenesulfonamide derivative useful as an intermediate in the preparation of the above 3-(substituted hydrazino)benzenesulfonamide of the formula (II), which is represented by the following formula (V'):

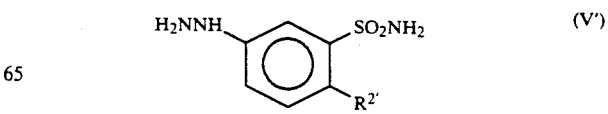

wherein $R^{2'}$ is H, $C_1-C_3$ alkyl or $C_1-C_4$ alkoxycarbonyl.

In a still further aspect of the invention, there is also provided a herbicidal composition comprising as an active ingredient the N-substituted-3-(substituted hydrazino)benzenesulfonamide derivative of the formula (I).

In a still further aspect of the invention, there is also provided a method for the control of monocotyledonous or dicotyledonous weeds on an agricultural or non-agricultural land, which comprises applying to the agricultural or non-agricultural land the N-substituted-3-(substituted hydrazino)benzenesulfonamide derivative of the formula (I) or a herbicidal composition comprising said derivative.

The N-substituted-3-(substituted hydrazino)-benzenesulfonamide derivatives of the present invention, which are represented by the formula (I), have not been disclosed in any publications known to the inventors of the present application, exhibit reliable herbicidal activity at low application dosages and show selectivity between crops and weeds. The herbicidal compositions of the invention, which contain the above derivatives as effective ingredients, are suitable particularly for controlling before or after germination dicotyledonous and/or monocotyledonous weeds in important crops, for example, such as wheat, rice, corn, soybean, cotton, beet, potato, tomato or the like. They are also usable for the control of weeds not only on agricultural lands such as upland fields, paddy fields and orchards but also on non-agricultural lands such as athletic fields and factory sites.

DETAILED DESCRIPTION OF PREFERRED EMBODIMENTS

Specific examples of the N-substituted-3-(substituted hydrazino)benzenesulfonamide derivative represented by the formula (I) in the invention include those shown in Table 1.

TABLE 1

| Compound No. | $R^1$ | $R^2$ | $X^1$ | $X^2$ | $Z$ |
|---|---|---|---|---|---|
| I-1 | $CF_3$ | H | $OCH_3$ | $OCH_3$ | CH |
| I-2 | COOH | H | $OCH_3$ | $OCH_3$ | CH |
| I-3 | $CF_3$ | Cl | $OCH_3$ | $OCH_3$ | CH |
| I-4 | COOH | Cl | $OCH_3$ | $OCH_3$ | CH |
| I-5 | $CF_3$ | $CH_3$ | $OCH_3$ | $OCH_3$ | CH |
| I-6 | COOH | $CH_3$ | $OCH_3$ | $OCH_3$ | CH |
| I-7 | $CF_3$ | $COOCH_3$ | $OCH_3$ | $OCH_3$ | CH |
| I-8 | COOH | $COOCH_3$ | $OCH_3$ | $OCH_3$ | CH |
| I-9 | $CF_3$ | $COOC_2H_5$ | $OCH_3$ | $OCH_3$ | CH |
| I-10 | COOH | $COOC_2H_5$ | $OCH_3$ | $OCH_3$ | CH |
| I-11 | $CF_3$ | $COOCH_3$ | Cl | $OCH_3$ | CH |
| I-12 | COOH | $COOCH_3$ | Cl | $OCH_3$ | CH |
| I-13 | $CF_3$ | $COOCH_3$ | $CH_3$ | $CH_3$ | CH |
| I-14 | COOH | $COOCH_3$ | $CH_3$ | $CH_3$ | CH |
| I-15 | $CF_3$ | $COOCH_3$ | $OCH_3$ | $CH_3$ | CH |
| I-16 | $CF_3$ | $COOCH_3$ | $OCH_3$ | $CH_3$ | N |
| I-17 | COOH | $COOCH_3$ | $OCH_3$ | $CH_3$ | N |
| I-18 | CCl=CClCOOH | Cl | $OCH_3$ | $OCH_3$ | CH |
| I-19 | CCl=CClCOOH | $COOCH_3$ | $OCH_3$ | $OCH_3$ | CH |
| I-20 | $CF_3$ | $COOCH_3$ | $OCH_3$ | $OCH_3$ | N |

The N-substituted-3-(substituted hydrazino)benzenesulfonamide derivatives represented by the formula (I) can each be synthesized by reacting a 3-(substituted hydrazino)benzenesulfonamide derivative of the formula (II) and a phenylcarbamate derivative of the following formula (III) in the presence of a base and in an organic solvent in accordance with the following reaction formula:

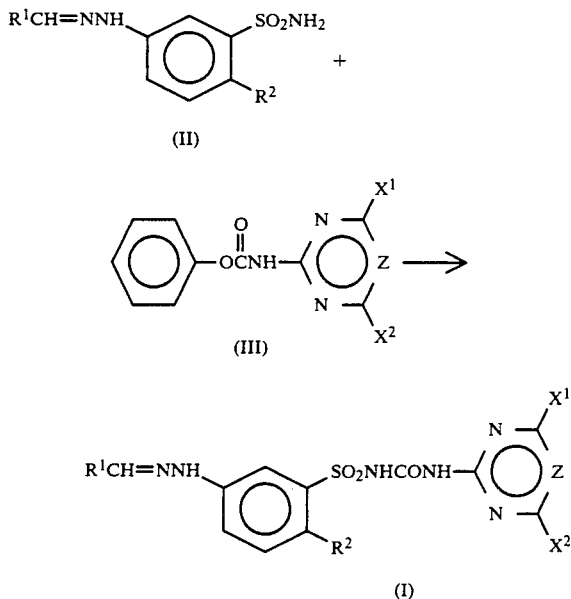

wherein $R^1$, $R^2$, $Z$, $X^1$ and $X^2$ have the same meanings as defined above.

In the above reaction, N,N-dimethylacetamide, N-methylpyrrolidone, acetonitrile or the like can be used as an organic solvent. On the other hand, diazabicyclooctane, diazabicyclononene, diazabicycloundecene or the like can be used as a base.

The reaction is conducted at a temperature in a range of from $-20°$ C. to $100°$ C., preferably from $0°$ C. to $50°$ C. for a reaction period in a range of from 0.5 hour to 24 hours.

After completion of the reaction, the reaction mixture is added to an aqueous solution of dilute hydrochloric acid and the precipitate thus formed is collected by filtration. The precipitate is dried in air and then purified by a purification technique such as reprecipitation or column chromatography or by a washing technique, whereby the intended N-substituted-3-(substituted hydrazino)benzenesulfonamide derivative represented by the formula (I) can be obtained with high purity.

The 3-(substituted hydrazino)benzenesulfonamide derivative represented by the formula (II), which is a preparation intermediate and is employed as the starting material in the above reaction, can be synthesized in accordance with the following reaction formula, using as a starting material a 3-aminobenzenesulfonamide derivative represented by the following formula (IV):

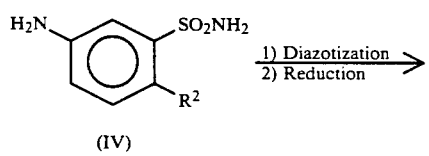

-continued

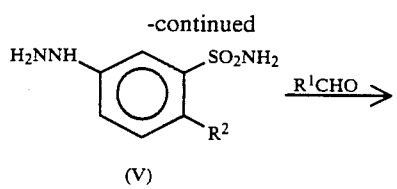

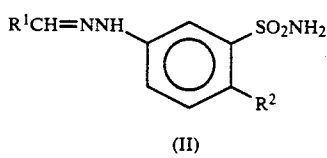

wherein $R^1$ and $R^2$ have the same meanings as defined above.

Synthesis of the compound represented by the formula (II) in accordance with the above-described reaction can be practiced in the following manner. The 3-hydrazinobenzenesulfonamide derivative represented by the formula (V)—which has been obtained by diazotizing the amino group of the compound represented by the formula (IV) and reducing the thus-diazotized derivative—is stirred together with trifluoroacetaldehyde ethylhemiacetal, glyoxylic acid monohydrate or mucochloric acid at 30°–120° C., preferably 70°–90° C. for 0.5–8 hours in acetic acid or propionic acid or at room temperature for 5–7 hours in 6N sulfuric acid. After completion of the reaction, the reaction product is collected from the reaction mixture by filtration or the reaction mixture is evaporated to dryness under reduced pressure and if necessary, is purified by washing, whereby the compound represented by the formula (II) can be obtained with good purity.

The compound represented by the formula (IV), which was used in the above reaction formula, can be obtained from the corresponding nitrobenzene derivative, for example, by using the process described in Bull. Chem. Soc. Jpn., 55, 3824 (1982); or from the corresponding 3-nitroaniline derivatives, for example, by the process described in Chem. Ber., 90, 841 (1957) or J. Macromol. Sci. Chem., 1969, 941, namely, by synthesizing 3-nitrobenzenesulfonamide derivatives and then reducing the nitro groups with $SnCl_2$ in methanol or ethanol containing 35% hydrochloric acid.

Further, the compound represented by the formula (III) can be obtained from phenyl chloroformate and the corresponding 2-amino-4,6-di-substituted pyrimidine (or 1,3,5-triazine), for example, by the process described in European Patent Specification No. 238,070.

Specific examples of the compound represented by the formulae (II) and useful as the above preparation intermediate are summarized in Table 2.

In addition, specific examples of the compound represented by the formula (V) are shown in Table 3.

TABLE 2

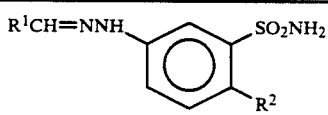

| Compound No. | $R^1$ | $R^2$ |
|---|---|---|
| II-1 | $CF_3$ | H |
| II-2 | COOH | H |
| II-3 | $CF_3$ | Cl |
| II-4 | COOH | Cl |
| II-5 | $CF_3$ | $CH_3$ |
| II-6 | COOH | $CH_3$ |
| II-7 | $CF_3$ | $COOCH_3$ |
| II-8 | COOH | $COOCH_3$ |
| II-9 | $CF_3$ | $COOC_2H_5$ |
| II-10 | COOH | $COOC_2H_5$ |
| II-11 | HOOCCCl=CCl— | Cl |
| II-12 | HOOCCCl=CCl— | $COOCH_3$ |

TABLE 3

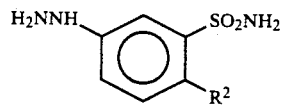

| Compound No. | $R^2$ |
|---|---|
| V-1 | H |
| V-2 | Cl |
| V-3 | $CH_3$ |
| V-4 | $COOCH_3$ |
| V-5 | $COOC_2H_5$ |

The N-substituted-3-(substituted hydrazino)benzenesulfonamide derivatives exhibit reliable herbicidal activity at low application dosages and show selectivity between crops and weeds. The herbicidal compositions of the invention, which contain the above compounds as effective ingredients, are therefore suitable for controlling either before or after emergence monocotyledonous weeds and/or dicotyledonous weeds in important crops such as wheat, rice, corn, soybean, cotton, beet, potato and tomato.

Exemplary dicotyledonous weeds which can be controlled by the herbicides of the invention include Amaranthus, Bidens, Stellaria, Solanum, Abutilon, Convolvulus, Matricaria, Galium, Lindernia, etc.

Illustrative monocotyledonous weeds include Echinochloa, Setaria, Digitaria, Avena, Cyperus, Alisma, Monochoria, etc.

The herbicidal compositions of the invention may take any preparation forms such as wettable powder, emulsion, powder, granule and the like. Known agronomically-acceptable vehicles (diluents) and aids can be used.

The applicable places of the herbicides according to the invention range from agricultural lands such as upland fields, paddy fields and orchard to non-agricultural lands such as athletic fields and factory sites. Examples:

The present invention will hereinafter be described by the following examples.

Synthesis Example 1

Synthesis of methyl 2-[(4,6-dimethoxypyrimidin-2-yl)aminocarbonylaminosulfonyl]-4-[(2,2,2-trifluoroethylidene)hydrazino]benzoate (Compound No. I-7)

At room temperature, 166 mg (0.5 mmol) of methyl 2-(aminosulfonyl)-4-[(2,2,2-trifluoroethlidene)hydrazino]-benzoate and 137.5 mg (0.5 mmol) of phenyl (4,6-dimethoxy-pyrimidin-2-yl)carbamate were dissolved in 1.5 ml of N,N-dimethylacetamide. Then, 86.1 mg of 1,8-diazabicyclo[5.4.0]undec-7-ene were added, followed by stirring for 5 minutes. The resultant mixture was allowed to stand for 15 hours. Thereafter, 0.2 ml of 35% hydrochloric acid was added to 20 ml of ice water, followed by the addition of the reaction mixture in 0.2 ml portions under stirring. After the reaction mixture was stirred for 20 minutes, the resulting precipitate was collected by filtration and dried in air. Using dichloromethane as an eluent, the crude product was purified by chromatography on a column of silica gel ("WAKO GEL C-300", trade name; product of Wako Pure Chemical Industries, Ltd.). The title compound was obtained as a white solid. Yield: 162 mg (64%). Melting point: 201°–202° C. Its physicochemical properties are shown in Table 4.

Synthesis Example 2

Synthesis of methyl 2-[(4,6-dimethoxy-1,3,5-triazin-2-yl)aminocarbonylaminosulfonyl]-4-[(2,2,2-trifluoroethylidene)hydrazino]benzoate (Compound No. I-20)

At room temperature, 166 mg (0.5 mmol) of methyl 2-(aminosulfonyl)-4-[(2,2,2-trifluoroethlidene)hydrazino]-benzoate and 138 mg (0.5 mmol) of phenyl (4,6-dimethoxy-1,3,5-triazin-2-yl)carbamate were dissolved in 1.5 ml of N,N-dimethylacetamide. Then, 86.1 mg of 1,8-diazabicyclo[5.4.0]undec-7-ene were added, followed by stirring for 5 minutes. The resultant mixture was allowed to stand for 6 hours. Thereafter, 0.2 ml of 35% hydrochloric acid was added to 30 ml of ice water, followed by the addition of the reaction mixture in 0.2 ml portions under stirring. After the reaction mixture was stirred for 20 minutes, the resulting precipitate was collected by filtration and dried in air. Using as an eluent a 1:9 mixed solvent of methyl acetate and benzene, the crude product was purified by chromatography on a column of silica gel ("WAKO GEL C-300", trade name; product of Wako Pure Chemical Industries, Ltd.). The title compound was obtained as a white solid. Yield: 103 mg (41%). Melting point: 117°–119° C. (foamed). Its physicochemical properties are shown in Table 4.

The other N-substituted-3-(substituted hydrazino)benzenesulfonamide derivatives shown in Table 1 were also synthesized in a similar manner to Synthesis Example 1. Namely, after obtaining crude products by a similar procedure to Synthesis Example 1, they were separately purified by chromatography on a silica gel column or washing. Physicochemical properties of each of the N-substituted-3-(substituted hydrazino)benzenesulfonamide derivatives are shown in Table 4. Incidentally, in Table 4 and in Tables 5 and 6 which will be given subsequently, the abbreviations in the columns for NMR data have the following meanings:

δ: (ppm), s: singlet, d: doublet, t: triplet,
q: quartet, m: multiplet, dd: double doublet,
br: broad.

Further, with respect to the individual N-substituted-3-(substituted hydrazino)benzenesulfonamide derivatives, the solvents employed upon purification thereof and the yields attained were as follows:

| Compound No. | Solvent employed | Yield (%) |
|---|---|---|
| Compounds purified by column chromatography: | | |
| I-1 | $CH_2Cl_2$ | 49 |
| I-7 | $CH_2Cl_2$ | 64 |
| I-9 | $CH_2Cl_2$ | 59 |
| I-11 | $CH_2Cl_2$ | 64 |
| I-13 | Methyl acetate + benzene | 67 |
| I-14 | Methyl acetate + benzene | 55 |
| I-15 | Methyl acetate + benzene | 24 |
| I-20 | Methyl acetate + benzene | 41 |
| Compounds purified by washing: | | |
| I-2 | $CH_2Cl_2$ | 68 |
| I-3 | petroleum ether | 93 |
| I-4 | $CH_2Cl_2$ + petroleum ether | 79 |
| I-5 | petroleum ether | 81 |
| I-6 | petroleum ether | 62 |
| I-8 | $CH_2Cl_2$ + petroleum ether | 70 |
| I-10 | $CH_2Cl_2$ | 50 |
| I-12 | $CH_2Cl_2$ + hexane | 80 |
| I-14 | $CH_2Cl_2$ + hexane | 70 |
| I-17 | $CH_2Cl_2$ + petroleum ether | 57 |
| I-18 | $CH_2Cl_2$ | 55 |
| I-19 | $CH_2Cl_2$ | 30 |

TABLE 4

| Compound No. | MS(m/e) *)(A) | MS(m/e) **)(B) | Melting Point or Decomposition Point (°C.) | IR (KBr, cm$^{-1}$) | | NMR (δ) |
|---|---|---|---|---|---|---|
| I-1 | 293 | 155 | 132–135 Decomposition | 3300–2700, 1710, 1610, 1570, 1490, 1450, 1370, 1250, 1160, 1120, 580 | CDCl$_3$ | 3.947(6H, s)5.783(1H, s)7.068(1H, q, 4.27Hz)7.443–7.738(5H, m)8.536(1H, s)12.701(1H, s) |
| I-2 | — | 155 | 168–170 Decomposition | 3350–2500, 1710, 1600, 1570, 1490, 1450, 1360, 1310, 1220, 1200, 1160, 580 | d$_6$-DMSO | 3.908(6H, s)5.990(1H, s)7.179(1H, s)7.374(1H, dd, 6.71Hz, 1.83Hz)7.482–7.533(2H, m)7.707(1H, s)10.548(1H, s)11.468(1H, s)12.594br(2H, s) |
| I-3 | 327 | 155 | 204–206 | 3420–2800, 1710, 1600, 1570, 1490, 1440, 1370, 1350, 1280, 1250, 1220 | d$_6$-DMSO | 3.898(6H, s)5.990(1H, s)7.29(1H, d, 7.3Hz)7.430(1H, q, 4.2Hz)7.59(1H, dd, 7.3Hz, 1.4Hz)7.797(1H, d, 1.4Hz)10.65br(1H, s)11.525(1H, s)13.019(1H, s) |
| I-4 | — | 155 | 146–147 Decomposition | 3300–2600, 1700, 1610, 1570, 1490, 1450, 1360, 1290, 1220, 1200, 1160, 1030, 820, 630, 580 | d$_6$-DMSO | 3.915(6H, s)6.020(1H, s)7.196(1H, s)7.372(1H, dd, 8.55Hz, 2.44Hz)7.580(1H, d, 8.55Hz)7.878(1H, d, 2.44Hz)10.665br(1H, s)11.559(1H, s)12.994br(1H, s) |
| I-5 | 307 | 155 | 187–189 Decomposition | 3300–2600, 3280, 2930, 1710, 1600, 1570, 1490, 1450, 1360, 1240, 1160, 1120, 760, 700, 590 | CDCl$_3$ | 2.585(3H, s)3.954(6H, s)5.805(1H, s)6.980(1H, q, 4.3Hz)7.221(1H, d, 8.5Hz)7.306(1H, s)7.394(1H, dd, 8.5Hz, 1.5Hz)7.719(1H, d, 1.5Hz)8.414(1H, s)12.735(1H, s) |
| I-6 | — | 155 | 149–152 Decomposition | 3250, 3150–2600, 1710, 1610, 1570, 1490, 1450, 1370, 1360, 1220, 1190, 1170, 590 | d$_6$-DMSO | 2.504(3H, s)3.911(6H, s)6.020(1H, s)7.155(1H, s)7.289–7.370(2H, m)7.782(1H, s)11.417(1H, s)12.508br(1H, s)12.728br(1H, s) |
| I-7 | 351 | 155 | 201–202 | 3400–2800, 3260, 3100, 2950, 1720, 1600, 1580, 1490, 1450, 1370, 1350, 1300, 1270, 1240, 1190, 1170, 1110, 890, 820, 630, 580 | d$_6$-DMSO | 3.762(3H, s)3.947(6H, s)6.010(1H, s)7.366(1H, d, 8Hz)7.494(1H, q, 4.9Hz)7.765(1H, d, 8Hz)7.855(1H, s)10.631(1H, s)11.771(1H, s)12.579(1H, s) |
| I-8 | — | 155 | 148–149 Decomposition | 3400–2700, 1710, 1600, 1570, 1440, 1370, 1350, 1270, 1230, 1210, 1190, 1160, 1110, 580 | d$_6$-DMSO | 3.795(3H, s)3.950(6H, s)6.010(1H, s)7.440(1H, dd, 8.55Hz, 1.83Hz)7.777(1H, d, 8.55Hz)7.903(1H, d, 1.83Hz)10.638(1H, s)11.783(1H, s)12.574(1H, s)12.750(1H, s) |
| I-9 | 365 | 155 | 125–128 Decomposition | 3320–2700, 3280, 1710, 1590, 1570, 1490, 1440, 1350, 1290, 1260, 1230, 1190, 1160, 1110, 630, 580 | CDCl$_3$ | 1.347(3H, t, 7.33Hz)4.010(6H, s)4.296(2H, q, 7.33Hz)5.790(1H, s)7.107(1H, d, 4.27Hz)7.457(1H, dd, 8.54Hz, 2.44Hz)7.491(1H, dd, 8.54Hz, 2.44Hz)7.780(1H, d, 2.44Hz)9.024(1H, s)12.662(1H, s)1.237(3H, t, 7.33Hz)3.945(6H, s)4.222(2H, q, 7.33Hz)6.003(1H, s) |
| I-10 | — | 155 | 138–140 Decomposition | 3300–2600, 1710, 1600, 1570, 1490, 1450, 1360, 1270, 1240, 1220, 1200, 1170, 580 | d$_6$-DMSO | 7.250(1H, s)7.431(1H, dd, 8.55Hz, 1.83Hz)7.770(1H, d, 8.55Hz)7.900(1H, d, 1.83Hz)10.634(1H, s)11.759(1H, s)12.555(1H, s)12.750br(1H, s) |
| I-11 | 351 | 159 | 144–146 Decomposed | 3340, 1740, 1610, 1580, 1470, 1375, 1310, 1290, 1190, 1130, 590 | CDCl$_3$ | 3.881(3H, s)4.147(3H, s)6.495(1H, s)7.169(1H, q, 3.66Hz)7.528(1H, dd, 8.55Hz, 2.44Hz)7.805(1H, d, 8.55Hz)7.872(1H, d, 2.44Hz)7.894(1H, s)8.966(1H, s)12.198(1H, s) |
| I-12 | — | 159 | 140–143 Decomposed | 3400–2800, 1730, 1590, 1580, 1450, 1360, 1295, 1275, 1125, 590 | d$_6$-DMSO | 3.788(3H, s)4.045(3H, s)6.879(1H, s)7.250(1H, s)7.442(1H, dd, 8.55Hz, 2.44Hz)7.792(1H, d, 8.55Hz)7.897(1H, d, 2.44Hz)10.902(1H, s)11.771(1H, s)11.95br(1H, s)12.750br(1H, s) |
| I-13 | 351 | 123 | 154–158 Decomposed | 3300–2700, 1730, 1720, 1620, 1480, 1470, 1450, 1360, 1310, 1290, 1260, 1130, 600 | CDCl$_3$ | 2.514(6H, s)3.878(3H, s)6.759(1H, s)7.190(1H, q, 3.06Hz)7.521(1H, dd, 8.54Hz, 2.44Hz)7.765(1H, d, 8.54Hz)7.889(1H, d, 2.44Hz)8.275(1H, s)9.269(1H, s)13.370(1H, s) |
| I-14 | — | 123 | 145–150 Decomposed | 3400–2600, 1750br, 1635, 1590, 1490, 1480, 1460, 1370, 1300, 1270, 1190, 1150, 610 | d$_6$-DMSO | 2.435(6H, s)3.757(3H, s)7.016(1H, s)7.245(1H, s)7.430(1H, dd, 7.94Hz)7.764(1H, d, 7.94Hz)7.886(1H, d, 1.83Hz)10.602(1H, s)11.761(1H, s)12.750br(1H, s)13.304(1H, s) |
| I-15 | 351 | 139 | 152–154 Decomposed | 3300–2800, 1750, 1610, 1620, 1590, 1470, 1450, 1370, 1310, 1280, 1260, 1130, 600 | CDCl$_3$ | 2.492(3H, s)3.866(3H, s), 3.986(3H, s)6.295(1H, s)7.158(1H, q, 3.05Hz)7.509(1H, dd, 8.54Hz, 2.44Hz)7.775(1H, d, 8.54Hz)7.792(1H, s)7.884(1H, d, 2.44Hz)9.227(1H, s)13.275(1H, s) |
| I-16 | 351 | 140 | 101–105 Decomposed | 3300–2800, 1730, 1610, 1570, 1450, 1360, 1300, 1270, 1240, 1170, 1110, 820, 590 | CDCl$_3$ | 2.633(3H, s)3.898(3H, s)4.086(3H, s)7.194(1H, q, 3.66Hz)7.526(1H, dd, 8.55Hz, 2.44Hz)7.804(1H, d, 8.55Hz)7.842(1H, s)8.235(1H, d, 2.44Hz)9.154(1H, s)12.615(1H, s) |

TABLE 4-continued

| Compound No. | MS(m/e) *(A) | MS(m/e) **(B) | Melting Point or Decomposition Point (°C.) | IR (KBr, cm$^{-1}$) | | NMR (δ) |
|---|---|---|---|---|---|---|
| I-17 | — | 140 | 144–146 Decomposed | 3350–2700, 1760, 1630, 1600, 1480, 1390, 1310, 1280, 1200, 1180, 1150, 850, 620 | d$_6$-DMSO | 2.500(3H, s)3.803(3H, s)3.996(3H, s)7.250(1H, s) 7.453(1H, dd, 8.54Hz, 2.44Hz)7.799(1H, d, 8.54Hz)7.891(1H, d, 2.44Hz) 11.085(1H, s)11.776(1H, s)12.513(1H, s)12.75(1H, s) |
| I-18 | — | 155 | 142–144 Decomposed | 3300–2700, 1720, 1600, 1580, 1540 1500, 1450, 1360, 1260, 1220, 1170, 1020, 810, 760, 690, 590 | d$_6$-DMSO | 3.915(6H, s)6.025(1H, s)7.321(1H, dd, 8.54Hz, 2.44Hz) 7.563(1H, d, 8.54Hz)7.831(1H, d, 2.44Hz)8.795(1H, s)10.697(1H, s) 11.666(1H, s)13.02br(1H, s) H of COOH was not observed. |
| I-19 | — | 155 | 148–149 Decomposed | 3300–2800, 1730, 1610, 1580, 1450, 1380, 1290, 1270, 1250, 1220, 1170, 1110, 1020, 590 | d$_6$-DMSO | 3.752(3H, s)3.947(6H, s)6.012(1H, s)7.370(1H, d, 8.55Hz) 7.764(1H, d, 8.55Hz)7.875(1H, s)8.830(1H, s)10.634(1H, s) 11.898(1H, s)12.577(1H, s) H of COOH was not observed. |
| I-20 | 351 | 156 | 117–119 Decomposed | 3300, 3200–2800, 1730, 1600, 1570, 1500, 1460, 1380, 1360, 1300, 1270, 1245, 1170, 1120, 815, 590 | CDCl$_3$ | 3.898(3H, s)4.110(6H, s)7.167(1H, q, 3.66Hz) 7.527(1H, dd, 8.55Hz, 1.33Hz)7.799(1H, d, 8.55Hz)7.845(1H, d, 1.83Hz) 8.111(1H, s)8.959(1H, s)12.261(1H, s) |

*)(A) 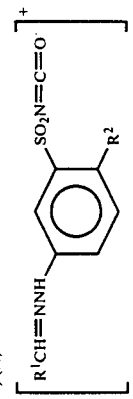

**)(B) 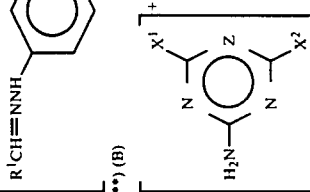

Synthesis Example 3

Synthesis of preparation intermediate, methyl 2-(aminosulfonyl)-4-(2,2,2-trifluoroethylidene)-hydrazino]benzoate (Compound No. II-7)

(1) Synthesis of methyl 2-(aminosulfonyl)-4-hydrazinobenzoate (Compound No. V-4):

To a mixture of 6 ml of 35% hydrochloric acid and 6 ml of water, 3 g of methyl 4-amino-2-(aminosulfonyl)-benzoate were added, followed by stirring at room temperature for 5 minutes. The reaction mixture was then cooled with ice water, followed by the addition of 3 ml of an aqueous solution of 0.95 g of sodium nitrite under stirring over 2 minutes to conduct diazotization.

In 6.52 ml of 35% hydrochloric acid, 6.78 g of stannous chloride were dissolved. The resulting solution was cooled with ice water and stirred, followed by the addition of the diazotized compound prepared above.

After the resultant mixture was stirred for 20 minutes, it was left over for 15 hours in a refrigerator. The reaction mixture was then transferred into a 3-l beaker, to which 38 g of sodium bicarbonate were then added under stirring to adjust the pH to 6. The mixture thus prepared was then extracted twice with 300 ml of methyl acetate. The extract was dried over sodium sulfate, and methyl acetate was distilled off to obtain a pale yellow solid. Yield: 2.76 g (86%). Melting point: 168°–170° C. Its physicochemical properties are shown in Table 6.

(2) Synthesis of methyl 2-(aminosulfonyl)-4-[(2,2,2-trifluoroethylidene)hydrazino]benzoate (Compound No. II-7):

In 4 ml of acetic acid, 367.5 mg (1.5 mmol) of the compound synthesized in the above procedure (1) (Compound No. V-4) and 0.21 ml of trifluoroacetaldehyde ethylhemiacetal were dissolved, followed by stirring at 80° C. for 3 hours. Acetic acid was then distilled off from the reaction mixture and 30 ml of ice water were added to the pale yellow residue. The insoluble matter was collected by filtration and then dried in air. The title compound was obtained as a pale yellow solid. Yield: 421 mg (86%). Its physicochemical properties are shown in Table 5.

The other compounds shown in Table 2 were also synthesized in accordance with the above reaction formula. Either the following reaction conditions (a) or (b) were employed.

(a) After reaction for 3–5 hours at 80° 90° C. in acetic acid in a flask, acetic acid was distilled off, and the reaction product was scraped out from the flask. As an alternative, the reaction product was washed out with a poor solvent from the flask, collected by filtration and then dried in air.

(b) After reaction for 5–7 hours at room temperature in 6N sulfuric acid, the insoluble matter was collected by filtration, washed with water and then dried in air [see Chem. Ber., 115, 3706-18 (1982)].

The following yields were achieved under the respective reaction conditions:

| Compound No. | Reaction conditions | Yield (%) |
| --- | --- | --- |
| II-1 | (a) (scraped out) | 98 |
| II-2 | (b) | 93 |
| II-3 | (b) | 76 |
| II-4 | (b) | 96 |
| II-5 | (b) | 40 |
| II-6 | (b) | 85 |
| II-7 | (a) water | 86 |
| II-8 | (a) $H_2O$/methanol (1/1) | 46 |
| II-9 | (a) $H_2O$/ethanol (1/1) | 58 |
| II-10 | (a) $H_2O$/acetonitrile (1/1) | 27 |
| II-11 | (b) | 75 |
| II-12 | (a) $H_2O, CH_2Cl_2$ | 32 |

The physicochemical properties of these compounds are shown in Table 5.

In addition, the physicochemical properties of the other compounds shown as preparation intermediates in Table 3 are given in Table 6.

TABLE 5

| Compound No. | MS (m/e) | Melting Point or Decomposition Point (°C.) | IR (KBr, cm$^{-1}$) | NMR ($\delta$) |
| --- | --- | --- | --- | --- |
| II-1 | 267 (M$^+$) | 150–155 | 3410, 3270, 1590, 1490, 1420, 1340, 1300, 1280, 1240, 1170, 1120, 1100, 900, 870, 780, 730, 680, 600, 590 | |
| II-2 | 199 (M$^+$ −44) | 188–190 Decomposed | 3300, 3200, 3250–2700, 1690, 1600, 1560, 1470, 1370, 1320, 1260, 1210, 1160, 980, 890, 800, 740, 680, 590, 520 | |
| II-3 | 301 (M$^+$) | 164–167 | 3410, 3280, 1600, 1470, 1400, 1340, 1300, 1290, 1270, 1250, 1170, 1140, 1110, 880, 830, 600 | |
| II-4 | 233 (M$^+$ −44) | 195–197 Decomposed | 3340, 3260, 3160, 3080, 3300–2700, 1690, 1600, 1560, 1460, 1380, 1370, 1340, 1310, 1260, 1230, 1160, 830, 770, 590 | |
| II-5 | 281 (M$^+$) | 168–169 Decomposed | 3310, 3230, 1625, 1610, 1520, 1490, 1410, 1350, 1290, 1250, 1160, 1140, 1120, 1070, 900, 830, 780, 700, 610, 510 | $d_6$-DMSO: 2.500(3H, s) 7.109(1H, dd, 8.5 Hz, 1.8 Hz) 7.270(1H, d, 8.5 Hz) 7.341(1H, q, 4.88 Hz) 7.377(2H, s) 7.614(1H, d, 1.8 Hz) 11.263(1H, s) |
| II-6 | | 172–173 Decomposed | 3370, 3250, 3100–2300, 1670, 1550, 1490, 1440, 1320, 1290, 1240, 1180, 1150, 1140, 870, 600 | $d_6$-DMSO: 2.507(3H, s) 7.138(1H, s) 7.183(1H, dd, 8.54 Hz, 2.44 Hz) 7.272(1H, d, 8.54 Hz) 7.367(2H, s) 7.657(1H, d, 2.44 Hz) 11.324(1H, s) H of COOH was not observed. |
| II-7 | 325 (M$^+$) | 227–230 Decomposed | 3350, 3280, 3250, 2950, 1700, 1690, 1600, 1540, 1440, 1330, 1300, 1280, 1260, 1170, 1150, 1110, 870, 780, 760, 590 | |
| II-8 | 257 (M$^+$ −44) | 197–200 Decomposed | 3200–2800br, 3250, 3150, 3080, 1710, 1690, 1600, 1560, 1320, 1300, 1270, 1240, 1160, 1120, 850, 830, 780, 590 | $d_6$-DMSO: 3.823(3H, s) 7.216(2H, s) 7.238(1H, s) 7.299(1H, dd, 7.93 Hz, 1.83 Hz) 7.737(1H, d, 7.93 Hz) 7.743(1H, d, 1.83 Hz) 11.666(1H, s) 12.645br(1H, s) |

TABLE 5-continued

| Compound No. | MS (m/e) | Melting Point or Decomposition Point (°C.) | IR (KBr, cm⁻¹) | NMR (δ) |
|---|---|---|---|---|
| II-9 | 339 (M+) | 238–241 Decomposed | 3350, 3280, 3250, 1680, 1600, 1330, 1300, 1280, 1240, 1170, 1150, 1110, 880, 780, 700, 600 | |
| II-10 | 271 (M+ −44) | 138–140 Decomposed | 3300–2700, 3250, 1710, 1690, 1600, 1560, 1320, 1270, 1240, 1160, 1120, 820, 780 | |
| II-11 | 353 (M+ −18) | 224–226 Decomposed | 3400, 3280, 3200–2700, 1670, 1610, 1510, 1460, 1340, 1270, 1170, 1020. | $d_6$-DMSO: 7.216(1H, dd, 8.55 Hz, 2.44 Hz) 7.497(1H, d, 8.55 Hz) 7.575(2H, s) 7.731(1H, d, 2.44 Hz) 8.764 (1H, s) 11.612(1H, s) H of COOH was not observed. |
| II-12 | 377 (M+ −18) | 239–241 Decomposed | 3380, 3260, 3200–2700, 1710, 1685, 1610, 1550, 1530, 1520, 1330, 1290, 1270, 1250, 1170, 1160, 1120, 1020, 745, 700 | $d_6$-DMSO: 3.823(3H, s) 7.223–7.760(5H, m) 8.822(1H, s) 11.832(1H, s) H of COOH was not observed. |

TABLE 6

| Compound No. | MS (m/e) | Melting Point or Decomposition Point (°C.) | IR (KBr, cm⁻¹) | NMR (δ) |
|---|---|---|---|---|
| V-1 | 187 | 113–116 | 3360, 3350, 3300, 3220, 1500, 1470, 1340, 1330, 1290, 1140, 1090, 780, 680, 580, 510 | |
| V-2 | 221 | 155–158 Decomposed | 3370, 3330, 3130, 2970, 1590, 1560, 1460, 1330, 1270, 1160, 970, 830, 740, 690, 590, 550, 510 | |
| V-3 | 201 | 161–164 | 3300, 3250, 3010, 1610, 1490, 1300, 1160, 1140, 920, 820, 690, 600, 520 | $d_6$-DMSO: 2.409(3H, s) 4.025br(2H, s) 6.840 (1H, dd, 8.5 Hz, 1.8 Hz) 6.901(1H, s) 7.048(2H, s) 7.349(1H, d, 1.8 Hz) |
| V-4 | 245 | 168–170 | 3350, 3310, 3250, 1680, 1630, 1590, 1440, 1350, 1330, 1300, 1270, 1170, 1160, 780, 700, 600 | |
| V-5 | 259 | 122–124 Decomposed | 3320, 3270, 2980, 1700, 1590, 1370, 1320, 1300, 1270, 1250, 1150, 1120, 770, 740, 700 | |

Compounds available in a similar manner to Synthesis Example 2 are summarized in Table 7.

TABLE 7

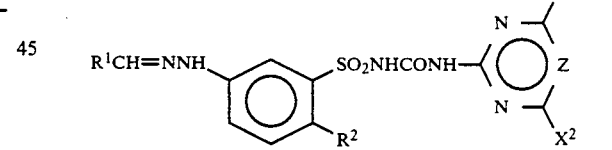

| Compound No. | R¹ | R² | X¹ | X² | Z |
|---|---|---|---|---|---|
| I-21 | CF₃ | H | CH₃ | OCH₃ | N |
| I-22 | CF₃ | H | OCH₃ | OCH₃ | N |
| I-23 | CF₃ | Cl | CH₃ | OCH₃ | N |
| I-24 | CF₃ | Cl | OCH₃ | OCH₃ | N |
| I-25 | CF₃ | CH₃ | CH₃ | OCH₃ | N |
| I-26 | CF₃ | CH₃ | OCH₃ | OCH₃ | N |
| I-27 | CF₃ | COOC₂H₅ | CH₃ | OCH₃ | N |
| I-28 | CF₃ | COOC₂H₅ | OCH₃ | OCH₃ | N |
| I-29 | COOH | H | OCH₃ | OCH₃ | N |
| I-30 | COOH | Cl | OCH₃ | OCH₃ | N |
| I-31 | COOH | CH₃ | CH₃ | OCH₃ | N |
| I-32 | COOH | COOCH₃ | OCH₃ | OCH₃ | N |
| I-33 | COOH | COOC₂H₅ | CH₃ | OCH₃ | N |
| I-34 | COOH | COOC₂H₅ | OCH₃ | OCH₃ | N |
| I-35 | CCl=CClCOOH | H | OCH₃ | OCH₃ | N |
| I-36 | CCl=CClCOOH | Cl | CH₃ | OCH₃ | N |
| I-37 | CCl=CClCOOH | CH₃ | OCH₃ | OCH₃ | N |
| I-38 | CCl=CClCOOH | COOCH₃ | CH₃ | OCH₃ | N |
| I-39 | CCl=CClCOOH | COOCH₃ | OCH₃ | OCH₃ | N |
| I-40 | CCl=CClCOOH | COOC₂H₅ | OCH₃ | OCH₃ | N |

Formulation examples and tests will hereinafter be described. It should be borne in mind that the vehicles (diluents) and aids, their mixing ratios and effective components can vary in wide ranges, respectively.

| Formulation Example 1: Wettable Powder | |
|---|---|
| Compound (Compound No. I-7) | 50 parts |
| A salt of ligninsulfonic acid | 5 parts |
| A salt of alkylsulfonic acid | 3 parts |
| Diatomaceous earth | 42 parts |

The above ingredients are mixed and ground into a wettable powder. For application, it is diluted with water.

| Formulation Example 2: Emulsion | |
|---|---|
| Compound (Compound No. I-11) | 25 parts |
| Xylene | 65 parts |
| Polyoxyethylene alkylaryl ether | 10 parts |

The above ingredients are mixed intimately into an emulsion. For application, it is diluted with water.

| Formulation Example 3: Granule | |
|---|---|
| Compound (Compound No. I-17) | 8 parts |
| Bentonite | 40 parts |
| Clay | 45 parts |
| A salt of ligninsulfonic acid | 7 parts |

The above ingredients are mixed intimately and after the addition of water, were kneaded and then formed into granules by an extruding granulator. They were then dried to provide a granular formulation, namely, a granule.

Test 1: Test on Herbicidal Activity by Foliar Application

Herbicidal solutions of each test compound, which had been prepared by dissolving at predetermined concentrations such a wettable powder of the test compound as that described in the above formulation example, and sprayed at dosages of 10 g/ha and 100 g/ha over foliar parts of *Amaranthus retroflexus* (Redroot pigweed), *Bidens pilosa* (Common blackjack), *Sinapis arvensis* (Wild mustard), *Stellaria media* (Common chickweed), *Cassia obtusifolia* (Sick-lepod), *Solanum nigrum* (Black nightshade), *Abutilon theophrasti* (Velvetleaf), *Convolvulus arvensis* (Field bindweed), *Matricaria chamomilla* (Wild chamomile), *Setaria viridis* (Green foxtail), *Echinochloa frumentaceum* (Barnyard grass), *Avena fatua* (Wild oat), and *Digitaria adscendens* (Henry crabgrass) which had been allowed to grow individually to 2-4 leaf stage in pots. Fourteen days later after spraying of the test compound, its herbicidal activity was evaluated in accordance with the below-described system. The results are summarized in Table 8.

Ranking system

Herbicidal activity

0: No effects
1: less than 31% of total kill
2: 31-50% of total kill
3: 51-70% of total kill
4: 71-90% of total kill
5: 91-100% of total kill

TABLE 8

| Compound No. | application dosage (g/ha) | A.r. | B.p. | S.a. | S.m. | C.o. | S.n. | A.t. | C.a. | M.c. | S.v. | E.f. | A.f. | D.a. |
|---|---|---|---|---|---|---|---|---|---|---|---|---|---|---|
| I-1 | 10 | 5 | 4 | 5 | 5 | 1 | 0 | 3 | 0 | 2 | 0 | 0 | 0 | 0 |
|  | 100 | 5 | 5 | 5 | 5 | 5 | 1 | 5 | 1 | 5 | 1 | 2 | 5 | 1 |
| I-2 | 10 | 5 | 4 | 5 | 5 | 2 | 0 | 5 | 1 | 5 | 2 | 0 | 0 | 0 |
|  | 100 | 5 | 5 | 5 | 5 | 5 | 4 | 5 | 5 | 5 | 4 | 4 | 0 | 0 |
| I-3 | 10 | 5 | 5 | 5 | 5 | 5 | 3 | 5 | 4 | 5 | 0 | 4 | 0 | 3 |
|  | 100 | 5 | 5 | 5 | 5 | 5 | 4 | 5 | 5 | 5 | 4 | 5 | 3 | 3 |
| I-4 | 10 | 5 | 5 | 5 | 5 | 5 | 1 | 5 | 1 | 5 | 0 | 0 | 2 | 0 |
|  | 100 | 5 | 5 | 5 | 5 | 5 | 5 | 5 | 5 | 5 | 5 | 5 | 5 | 3 |
| I-5 | 10 | 5 | 5 | 5 | 5 | 5 | 4 | 5 | 0 | 5 | 0 | 2 | 0 | 0 |
|  | 100 | 5 | 5 | 5 | 5 | 5 | 5 | 5 | 3 | 5 | 2 | 5 | 0 | 2 |
| I-6 | 10 | 5 | 5 | 5 | 5 | 5 | 5 | 5 | 5 | 5 | 3 | 2 | 2 | 2 |
|  | 100 | 5 | 5 | 5 | 5 | 5 | 5 | 5 | 5 | 5 | 5 | 4 | 3 | 3 |
| I-7 | 10 | 5 | 5 | 5 | 5 | 5 | 5 | 5 | 4 | 5 | 5 | 5 | 3 | 0 |
|  | 100 | 5 | 5 | 5 | 5 | 5 | 5 | 5 | 5 | 5 | 5 | 5 | 5 | 5 |
| I-8 | 10 | 5 | 5 | 5 | 5 | 5 | 5 | 5 | 5 | 5 | 5 | 5 | 5 | 0 |
|  | 100 | 5 | 5 | 5 | 5 | 5 | 5 | 5 | 5 | 5 | 5 | 5 | 5 | 5 |
| I-9 | 10 | 5 | 5 | 5 | 5 | 5 | 5 | 5 | 5 | 5 | 5 | 2 | 4 | 0 |
|  | 100 | 5 | 5 | 5 | 5 | 5 | 5 | 5 | 5 | 5 | 5 | 5 | 5 | 4 |
| I-10 | 10 | 5 | 5 | 5 | 5 | 5 | 5 | 5 | 5 | 5 | 3 | 4 | 4 | 0 |
|  | 100 | 5 | 5 | 5 | 5 | 5 | 5 | 5 | 5 | 5 | 5 | 5 | 5 | 3 |
| I-11 | 10 | 5 | 5 | 5 | 5 | 5 | 5 | 5 | 3 | 5 | 4 | 5 | 0 | 0 |
|  | 100 | 5 | 5 | 5 | 5 | 5 | 5 | 5 | 5 | 5 | 5 | 5 | 5 | 2 |
| I-12 | 10 | 5 | 5 | 5 | 5 | 5 | 5 | 5 | 5 | 5 | 5 | 4 | 0 | 0 |
|  | 100 | 5 | 5 | 5 | 5 | 5 | 5 | 5 | 5 | 5 | 5 | 5 | 5 | 3 |
| I-13 | 10 | 5 | 5 | 5 | 5 | 5 | 5 | 5 | 5 | 5 | 5 | 5 | 5 | 0 |
|  | 100 | 5 | 5 | 5 | 5 | 5 | 5 | 5 | 5 | 5 | 5 | 5 | 5 | 5 |
| I-14 | 10 | 5 | 5 | 5 | 5 | 5 | 5 | 5 | 5 | 5 | 5 | 5 | 5 | 5 |
|  | 100 | 5 | 5 | 5 | 5 | 5 | 5 | 5 | 5 | 5 | 5 | 5 | 5 | 5 |
| I-15 | 10 | 5 | 5 | 5 | 5 | 5 | 5 | 5 | 5 | 5 | 5 | 4 | 5 | 1 |
|  | 100 | 5 | 5 | 5 | 5 | 5 | 5 | 5 | 5 | 5 | 5 | 5 | 5 | 5 |
| I-16 | 10 | 5 | 5 | 5 | 5 | 5 | 5 | 5 | 5 | 5 | 4 | 2 | 2 | 0 |
|  | 100 | 5 | 5 | 5 | 5 | 5 | 5 | 5 | 5 | 5 | 5 | 5 | 5 | 3 |
| I-17 | 10 | 5 | 5 | 5 | 5 | 5 | 5 | 5 | 5 | 5 | 5 | 1 | 2 | 0 |
|  | 100 | 5 | 5 | 5 | 5 | 5 | 5 | 5 | 5 | 5 | 5 | 5 | 5 | 5 |
| I-18 | 10 | 5 | 5 | 5 | 5 | 3 | 3 | 5 | 5 | 5 | 2 | 0 | 0 | 0 |
|  | 100 | 5 | 5 | 5 | 5 | 5 | 5 | 5 | 5 | 5 | 4 | 4 | 4 | 0 |
| I-19 | 10 | 5 | 5 | 5 | 5 | 4 | 4 | 5 | 5 | 5 | 3 | 1 | 1 | 0 |
|  | 100 | 5 | 5 | 5 | 5 | 5 | 5 | 5 | 5 | 5 | 4 | 4 | 4 | 1 |
| I-20 | 10 | 5 | 5 | 5 | 5 | 5 | 5 | 5 | 5 | 5 | 4 | 2 | 2 | 0 |

TABLE 8-continued

| Compound No. | application dosage (g/ha) | A.r. | B.p. | S.a. | S.m. | C.o. | S.n. | A.t. | C.a. | M.c. | S.v. | E.f. | A.f. | D.a. |
|---|---|---|---|---|---|---|---|---|---|---|---|---|---|---|
| | 100 | 5 | 5 | 5 | 5 | 5 | 5 | 5 | 5 | 5 | 5 | 5 | 5 | 4 |

Note
A.r.: *Amaranthus retroflexus*
B.p.: *Bidens pilosa*
S.a.: *Sinapis arvensis*
S.m.: *Stellaria media*
C.o.: *Cassia obtusifolia*
S.n.: *Solanum nigrum*
A.t.: *Abutilon theophrasti*
C.a.: *Convolvulus arvensis*
M.c.: *Matricaria chamomilla*
S.v.: *Setaria viridis*
E.f.: *Echinochloa frumentaceum*
A.f.: *Avena fatua*
D.a.: *Digitaria adscendens*

Test 2: Germination Test of Seeds

Two sheets of filter paper were placed in a superposed relation in each of Petri dishes having a diameter of 9 cm. Water suspensions of each test compound (concentrations of the active ingredient: 1 ppm and 50 ppm) were separately poured in an amount of 5 ml per dish into the Petri dishes. Seeds of *Amaranthus retroflexus* (Redroot pigweed), *Bidens pilosa* (Common blackjack), *Matricaria chamomilla* (Wild chamomile), *solanum nigrum* (Black nightshade), *Echinochloa oryzicola* (Barnyard grass), *Cyperus iria* (Rice flatsedge) and *Setaria viridis* (Green foxtail) were placed at a rate of 10 seeds per dish in the Petri dishes. They were thereafter allowed to germinate in a constant-temperature chamber at 28° C. Fourteen days later after placement in the Petri dishes, the degrees of germination and growth inhibition were observed visually. The observation results were ranked in accordance with the below-described 6-stage system. The results are summarized in Table 9.

Growth inhibition rate

0: No inhibition
1: less than 31%
2: 31–50%
3: 51–70%
4: 71–90%
5: 91–100%

TABLE 9

| Compound No. | Concentration (ppm) | A.r. | B.p. | M.c. | S.n. | E.o. | C.i. | S.v. |
|---|---|---|---|---|---|---|---|---|
| I-1 | 1 | 3 | 3 | 4 | 1 | 4 | 3 | 2 |
| | 50 | 5 | 4 | 4 | 5 | 4 | 4 | 4 |
| I-2 | 1 | 3 | 0 | 3 | 3 | 0 | 3 | 1 |
| | 50 | 4 | 4 | 4 | 4 | 3 | 4 | 5 |
| I-3 | 1 | 3 | 3 | 4 | 2 | 4 | 3 | 4 |
| | 50 | 4 | 3 | 4 | 5 | 5 | 4 | 5 |
| I-4 | 1 | 4 | 3 | 4 | 3 | 4 | 3 | 3 |
| | 50 | 4 | 4 | 4 | 5 | 5 | 4 | 5 |
| I-5 | 1 | 2 | 0 | 2 | 2 | 2 | 3 | 2 |
| | 50 | 3 | 3 | 3 | 3 | 5 | 4 | 5 |
| I-6 | 1 | 3 | 2 | 3 | 2 | 3 | 2 | 3 |
| | 50 | 5 | 4 | 3 | 4 | 4 | 3 | 4 |
| I-7 | 1 | 3 | 3 | 4 | 3 | 4 | 5 | 5 |
| | 50 | 3 | 4 | 4 | 5 | 5 | 5 | 5 |
| I-8 | 1 | 4 | 3 | 5 | 3 | 5 | 5 | 5 |
| | 50 | 4 | 4 | 5 | 3 | 5 | 5 | 5 |
| I-9 | 1 | 4 | 4 | 5 | 4 | 4 | 4 | 3 |
| | 50 | 5 | 4 | 5 | 4 | 5 | 5 | 5 |
| I-10 | 1 | 3 | 3 | 5 | 4 | 1 | 4 | 4 |
| | 50 | 4 | 4 | 5 | 4 | 4 | 4 | 5 |
| I-11 | 1 | 2 | 1 | 1 | 5 | 1 | 2 | 1 |
| | 50 | 4 | 4 | 3 | 5 | 3 | 4 | 4 |
| I-12 | 1 | 2 | 0 | 4 | 1 | 1 | 3 | 1 |
| I-13 | | 3 | 2 | 4 | 5 | 2 | 4 | 3 |
| | 1 | 3 | 2 | 4 | 1 | 2 | 2 | 2 |
| | 50 | 4 | 4 | 4 | 5 | 4 | 4 | 4 |
| I-14 | 1 | 2 | 1 | 1 | 1 | 1 | 1 | 1 |
| | 50 | 3 | 3 | 4 | 4 | 3 | 4 | 4 |
| I-15 | 1 | 3 | 2 | 3 | 2 | 1 | 4 | 3 |
| | 50 | 4 | 4 | 5 | 3 | 4 | 4 | 4 |
| I-16 | 1 | 1 | 0 | 3 | 2 | 0 | 2 | 1 |
| | 50 | 3 | 3 | 4 | 4 | 4 | 4 | 5 |
| I-17 | 1 | 1 | 1 | 2 | 2 | 0 | 2 | 0 |
| | 50 | 2 | 2 | 3 | 4 | 1 | 4 | 3 |
| I-18 | 1 | 3 | 2 | 3 | 3 | 4 | 4 | 4 |
| | 50 | 4 | 3 | 5 | 3 | 5 | 4 | 5 |
| I-19 | 1 | 3 | 2 | 4 | 2 | 3 | 3 | 4 |
| | 50 | 4 | 3 | 4 | 4 | 5 | 4 | 4 |
| I-20 | 1 | 1 | 1 | 3 | 2 | 0 | 2 | 1 |
| | 50 | 3 | 3 | 4 | 4 | 3 | 4 | 4 |

Note
A.r.: *Amaranthus retroflexus*
B.p.: *Bidens pilosa*
M.c.: *Matricaria chamomilla*
S.n.: *Solanum nigrum*
E.o.: *Echinochloa oryzicola*
C.i.: *Cyperus iria*
S.v.: *Setaria viridis*

We claim:

1. An N-substituted-3-(substituted hydrazino)-benzenesulfonamide derivative of the formula (I):

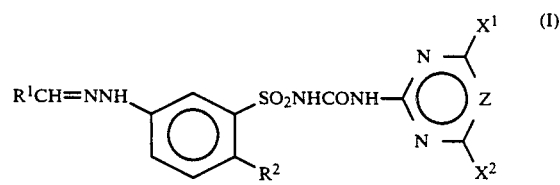

wherein $R^1$ is $CF_3$, COOH or $CCl=CClCOOH$, $R^2$ is H, Cl, $C_1$–$C_3$ alkyl or $C_1$–$C_4$ alkoxycarbonyl; Z is N; $X^1$ is $C_1$–$C_3$ alkyl, $C_1$–$C_3$ alkoxyl or Cl; and $X^2$ is $C_1$–$C_3$ alkyl or $C_1$–$C_3$ alkoxyl.

2. A derivative of claim 1, wherein $R^1$ is $CF_3$, COOH or $CCl=CClCOOH$, $R^2$ is H, Cl, $CH_3$, $COOCH_3$ or $COOC_2H_5$, Z is N, $X^1$ is $OCH_3$, and $X^2$ is $OCH_3$.

3. A derivative of claim 1, wherein $R^1$ is $CF_3$ or COOH, $R^2$ is $COOCH_3$, Z is N, $X^1$ is Cl, and $X^2$ is $OCH_3$.

4. A derivative of claim 1, wherein $R^1$ is $CF_3$ or COOH, $R^2$ is $COOCH_3$, Z is N, $X^1$ is $CH_3$ or $OCH_3$, and $X^2$ is $CH_3$.

5. A derivative of claim 1, wherein $R^2$ is Cl or $COOCH_3$, Z is N, $X^1$ is $OCH_3$, and $X^2$ is $OCH_3$.

6. A derivative of claim 1, wherein $R^1$ is $CF_3$ or COOH, $R^2$ is $COOCH_3$, Z is N, $X^1$ is $OCH_3$, and $X^2$ is $CH_3$ or $OCH_3$.

7. A herbicidal composition comprising a herbicidally effective amount of an N-substituted-3-(substituted hydrazino)benzenesulfonamide derivative of claim 1 nd an agronomically-acceptable vehicle or diluent.

8. A method for the control of monocotyledonous or dicotyledonous weeds on an agricultural or non-agricultural land, which comprises applying to the agricultural or non-agricultural land an N-substituted-3-(substituted hydrazino)benzenesulfonamide derivative of claim 1 or a herbicidal composition comprising said derivative.

* * * * *